United States Patent
Wyrsta et al.

(10) Patent No.: US 9,499,881 B2
(45) Date of Patent: Nov. 22, 2016

(54) REFINING METHODS AND AGENTS FOR RARE EARTH PRODUCTION

(71) Applicant: Lixivia, Inc., Santa Barbara, CA (US)

(72) Inventors: Michael D. Wyrsta, Santa Barbara, CA (US); Zachary J. A. Komon, San Diego, CA (US)

(73) Assignee: LIXIVIA, INC., Santa Barbara, CA (US)

( * ) Notice: Subject to any disclaimer, the term of this patent is extended or adjusted under 35 U.S.C. 154(b) by 161 days.

(21) Appl. No.: 14/096,129

(22) Filed: Dec. 4, 2013

(65) Prior Publication Data
US 2014/0154155 A1  Jun. 5, 2014

Related U.S. Application Data (60) Provisional application No. 61/797,355, filed on Dec. 4, 2012.

(51) Int. Cl.
*C22B 59/00* (2006.01)
*C22B 3/28* (2006.01)

(52) U.S. Cl.
CPC ............ *C22B 59/00* (2013.01); *C22B 3/001* (2013.01); *Y02P 10/234* (2015.11)

(58) Field of Classification Search
None
See application file for complete search history.

(56) References Cited

U.S. PATENT DOCUMENTS

| 5,939,034 A | 8/1999 | Virnig et al. |
| 6,951,960 B2 | 10/2005 | Perraud |

FOREIGN PATENT DOCUMENTS

| EP | 1309392 | 7/2006 |
| JP | 2005-97072 | 4/2005 |
| SU | 340262 a | * 9/1974 |
| SU | 1370076 A | * 1/1988 |
| WO | 2012/055750 | 5/2012 |

OTHER PUBLICATIONS

Kodama, S. et al, "Development of a new pH-swing $CO_2$ mineralization process with a recyclable reaction solution", Energy, 2008, vol. 33, pp. 776-784.

* cited by examiner

*Primary Examiner* — Melissa Swain
(74) *Attorney, Agent, or Firm* — Fish & Tsang, LLP (57) ABSTRACT

Hydrometallurgical systems, methods, and compositions are described in which organic amine-based lixiviants are utilized in the selective recovery of rare earth elements. The lixiviant can be regenerated in situ, permitting the organic amine to be used in substoichiometric amounts.

22 Claims, 4 Drawing Sheets

REFINING METHODS AND AGENTS FOR RARE EARTH PRODUCTION

This application claims priority to U.S. Provisional Application No. 61/797,355 filed on Dec. 4, 2012. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is hydrometallurgy, particularly as it is related to the extraction or recovery of rare earth elements or lanthanides.

BACKGROUND

Rare earth elements, also known as the lanthanide family of elements, are commercially valuable metals that are generally present in low abundance in commercially accessible ores, and often are often found with undesirable contaminating elements (for example, thorium). In a typical process for isolation of a member of the lanthanide family, hot sodium hydroxide at high concentrations is used to generate soluble lanthanide hydroxide and thorium hydroxide from ore. The mixture of hydroxides is then treated with hydrochloric acid to generate lanthanide chlorides, which are soluble and remain in solution, and a sludge of thorium hydroxide (which has reduced solubility at the altered pH). Unfortunately, this process can leave significant amounts of thorium in solution following acid treatment. Since this element is radioactive significant further refinement steps are necessary to assure its removal, adding significantly to processing costs. In addition, the use of a strong base at an elevated temperature both presents a hazard to workers and requires the use of specialized equipment. Thus there is a pressing need for efficient, effective, and scalable methods for the isolation of rare earth elements at high purity.

Numerous approaches have been devised to attempt to address these issues. Hydrometallurgy, or the extraction of metals from ores through treatment with lixiviant solutions (i.e. lixiviants) is one approach that has been used successfully for the isolation of metals from a variety of minerals and other sources. In typical hydrometallurgical processes ore is crushed or pulverized to increase surface area prior to exposure to a lixiviant, which contains compounds that render the metal soluble in the solution and leave behind undesirable contaminants. Following collection of the solution the metal can be recovered from the solution by various means, such as by electrodeposition or by precipitation from the solution. Commercial development of hydrometallurgical processes, however, is often hindered by the expenses involved in production and use of the lixiviant, efficient recovery of the desired metal, and difficulties in adapting current commercial plants.

In an approach disclosed in U.S. Pat. No. 5,939,034 (to Virnig and Michael), metals are solubilized in an aqueous lixiviant containing ammoniacal thiosulfate and extracted into an immiscible organic phase containing guanidyl or quaternary amine compounds. Metals are then recovered from the organic phase by electroplating. A similar approach is disclosed in U.S. Pat. No. 6,951,960 (to Perraud) in which metals are extracted from an aqueous phase into an organic phase that contains an amine chloride. The organic phase is then contacted with a chloride-free aqueous phase that extracts metal chlorides from the organic phase. Amines are then regenerated in the organic phase by exposure to aqueous hydrochloric acid. Such approaches, however, are hindered by the use of volatile amines in the lixiviant, and necessarily involve the use of expensive and potentially toxic organic solvents.

In a related approach, European Patent Application No. EP1309392 (to Kocherginsky and Grischenko) discloses a membrane-based method in which copper is initially complexed with ammonia or organic amines. The copper:ammonia complexes are captured in an organic phase contained within the pores of a porous membrane, and the copper is transferred to an extracting agent held on the opposing side of the membrane. While such an approach minimizes the use of organic solvent, it requires the use of complex equipment that is not readily adaptable to current processing facilities. In addition, the capacity of such a process is necessarily limited by the available surface area of the membrane.

Kodama et al. (Energy 33(2008), 776-784) disclose a method for $CO_2$ capture using calcium silicate ($2CaO.SiO_2$) and a solution of ammonium chloride ($NH_4Cl$). This reaction forms soluble calcium chloride ($CaCl_2$), which is reacted with carbon dioxide ($CO_2$) under alkaline conditions to form insoluble calcium carbonate ($CaCO_3$) that captures $CO_2$ while releasing chloride ions (Cl–). Japanese Patent Application No. 2005097072 (to Katsunori and Tateaki) discloses a similar method for $CO_2$ capture, in which ammonium chloride ($NH_4Cl$) is dissociated into ammonia gas ($NH_3$) and hydrochloric acid (HCl), the HCl being utilized to generate calcium chloride ($CaCl_2$) that is mixed with ammonium hydroxide ($NH_4OH$) for $CO_2$ capture. Kodama et al. and Katsunori and Tateaki, however, fail to recognize hydrometallurgical applications of such reactions, and rare earth elements are not considered. In addition, the loss of highly volatile ammonia during processing results in both inefficiencies and the need for specialized equipment to reduce environmental impact.

International Application WO 2012/055750 (to Tavakkoli et al.) discloses a method for purifying calcium carbonate ($CaCO_3$), in which $CaCO_3$ from high content sources is converted to calcium oxide (CaO) by calcination. The resulting CaO is treated with an ammonium chloride ($NH_4Cl$) solution to produce calcium chloride ($CaCl_2$), which is subsequently reacted with high purity carbon dioxide ($CO_2$) to produce $CaCO_3$ and $NH_4Cl$. High purity $CaCO_3$ is subsequently recovered from the solution by crystallization using seed crystals. Tavakkoli et al., however, does not consider rare earth elements, and it is not clear if such an approach can be used with low content or highly contaminated starting materials. In addition, utilization on a large scale would require capturing or containing the highly volatile ammonia gas that results from such a process.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for scalable hydrometallurgical methods that provides simple and economical isolation of rare earth elements.

SUMMARY OF THE INVENTION

The inventive subject matter provides apparatus, systems and methods in which hydrometallurgical processes utilizing lixiviants that contain organic amine cation/counterion anion complexes are used to recover rare earth elements. The organic amine component of the lixiviant is selected to provide selective solubilization of salts of rare earth elements. The organic amine cation/counterion anion complex transfers counterions to rare earth hydroxides, generating soluble rare earth/counterion complexes and uncharged organic amines. The organic amine cation/counterion anion complex is regenerated by the addition of an acid, permitting the organic amine to act as a pseudocatalyst that can be used in substoichiometric amounts.

One group of embodiments of the inventive concept are methods for extracting rare earth elements, in which a sample is mixed or otherwise contacted with a lixiviant that contains an organic amine in the form of an organic amine cation paired with a counterion. In some embodiments the lixiviant is formed in situ by adding an acid to an uncharged organic amine that is in contact with the sample. The organic amine is preferably a weak base, and can be obtained from a biological source. A supernatant is formed that includes a soluble rare earth cation complexed with the counterion and uncharged organic amine. The organic amine cation is regenerated by the addition of an acid, thereby regenerating the lixiviant. In preferred embodiments the organic amine cation is regenerated during extraction of the rare earth metal, allowing the organic amine to be used in substoichiometric amounts.

Another group of embodiments of the inventive concept are methods for sequentially recovering two or more rare earth elements from a sample using organic amine containing lixiviants. A sample containing two or more rare earth elements is contacted with a first lixiviant (i.e. a solution containing a first organic amine and a first counterion) resulting in a first supernatant and a depleted sample. The first supernatant includes an uncharged first organic amine and a first complex, which includes a first rare earth element cation and a first counterion. The first rare earth element cation is transferred from the depleted sample, for example by removing the first supernatant, and the depleted sample is further processed. The depleted sample can be contacted with a second lixiviant, which includes a second organic amine cation and a second counterion. This yields a second supernatant, which includes an uncharged second organic amine and a second complex, which includes a second alkaline earth element cation and a second counterion. The second rare earth element is recovered by transferring the second rare earth cation from the second supernatant. In some embodiments of the inventive concept the first organic amine cation is regenerated by the addition of an acid, which regenerates the first lixiviant. Similarly, the second organic amine cation is regenerated by the addition of an acid, which regenerates the second lixiviant. In a preferred embodiment the first lixiviant and the second lixiviant can be regenerated during their respective extraction steps, permitting the related organic amine to be used in substoichiometric amounts.

Yet another group of embodiments of the inventive concept are methods for extracting two or more rare earth elements simultaneously from a sample using an organic amine containing lixiviant. In such embodiments a sample containing two or more rare earth elements is contacted with a lixiviant solution that includes a first organic amine cation, a second organic amine cation, and a counterion. In some embodiments of the inventive concept, the first organic amine cation and the second organic amine cation are the same species; in other embodiments of the inventive concept the first organic amine cation and the second organic amine cation are different species. The resulting first supernatant includes an uncharged first organic amine, an uncharged second organic amine, a first complex (i.e. a first rare earth metal cation complexed with a counterion) and a second complex (i.e. a second rare earth metal cation complexed with a counterion). A second supernatant is subsequently formed by transferring the first rare earth metal cation from the first supernatant, for example by selective precipitation of the first rare earth element with a first precipitant. The second rare earth metal cation is then transferred from this second supernatant, for example by precipitation of the second rare earth element with a second precipitant. The first organic amine cation and the second organic amine cation, and therefore the lixiviant, are regenerated during these processes. In preferred embodiments of the inventive concept the first organic amine cation and the second organic amine cation are regenerated by the addition of an acid during the extraction process, thereby permitting the first organic amine and the second organic amine to be used in substoichiometric amounts. In some of these embodiments the first precipitant and the second precipitant are different species chosen to selectively precipitate the first rare earth element and the second rare earth element, respectively. In other embodiments the first precipitant and the second precipitant are the same species utilized at different concentrations or at different temperatures.

Various objects, features, aspects and advantages of the inventive subject matter will become more apparent from the following detailed description of preferred embodiments, along with the accompanying drawing figures in which like numerals represent like components.

DETAILED DESCRIPTION

Throughout the following discussion, numerous references will be made regarding lixiviants. A lixiviant should be understood to be a chemical entity that has the ability to selectively extract metals or metal ions from inorganic or organic solids in an aqueous or other solvent mixture. Within the context of this patent the term organic amine encompasses ammonia and ammonia derivatives in addition to nitrogen containing organic compounds.

Hydrometallurgical methods, such as leaching, have long been used to recover commercially valuable metals from low yield sources, such as mine tailings. Inventors have discovered a hydrometallurgical method for the recovery of rare earth elements (i.e. rare earth metals), such as members of the lanthanide family, through the use of lixiviants that include organic amines. In addition inventors have determined that such organic amine-based lixiviants can be regenerated during and/or after processing, permitting the organic amines to act in a pseudocatalytic manner. This pseudocatalytic behavior allows the organic amines to be applied in substoichiometric amounts. In addition, the selectivity of certain organic amines can permit stepwise isolation of different rare earth elements from the same sample.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The following discussion provides many exemplary embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Embodiments of the inventive process can include at least one compound of the general composition depicted in Compound 1 for use with any source of material that contains one or more a form(s) of a lanthanide hydroxide forming species, that can be hydrated to form Ln(OH)x or other hydrated species that would react with lixiviants of the form found in Compound 1. Such hydrated forms may be present in the material as it is obtained from nature or can be introduced by processing (for example through treatment with a base or by oxidation), and can be stable or transient. Selective extraction of the desired lanthanide can be based on the presence of a metal hydroxide that has a stronger basicity than the organic amine-based lixiviants used in the extraction process. In addition, an organic amine based lixiviant and counterion can be selected that permit use of the organic amine in substoichiometric amounts (i.e. as a pseudocatalyst).

Organic amines of the inventive concept have the general formula shown in Compound 1, where N is nitrogen, H is hydrogen, and X is a counterion (i.e. a counter anion).

Compound 1

Suitable counterions can have a pKa ranging from about 1 to about 7, and can be any form or combination of atoms or molecules that produce the effect of a negative charge. Counterions can halides (for example fluoride, chloride, bromide, and iodide), anions derived from mineral acids (for example nitrate, phosphate, bisulfate, sulfate, silicates, carbonate, and bicarbonate), cations derived from organic acids (for example carboxylate citrate, malate, acetate, thioacetate, propionate and, lactate), organic molecules or biomolecules (for example acidic proteins or peptides, amino acids, nucleic acids, and fatty acids), and others (for example zwitterions and basic synthetic polymers). For example, ammonium chloride ($NH_4Cl$) conforms to Compound 1 where there is one nitrogen ($N_1$), $R_1$, $R_2$, and $R_3$ are hydrogen, and there is one counter anion ($X_1$), which is chloride (Cl−). Compounds having the general formula shown in Compound 1 can have a wide range of acidities, and an organic amine of the inventive concept can be selected on the basis of its acidity so that it can selectively react with one or more rare earth metal salts or oxides from a sample containing a mixture of rare earth metal salts or oxides. Such a compound, when dissolved in water or another suitable solvent, can (for example) effectively extract the rare earth element cerium presented in the form cerium hydroxide in a suitable sample (e.g. alkaline opened monazite). Equation 1 depicts a primary chemical reaction in extracting an insoluble lanthanide salt (in this instance a hydroxide salt) from a matrix using an organic amine cation (OA-H+)/counterion (CI−) complex (OA-H+/CI−) as a lixiviant. Note that the OA-H+/CI− complex dissociates in water into OA-H+ and CI−.

Equation 1

The counterion (CI−) is transferred from the organic amine cation (OA-H+) to the lanthanide salt to form a soluble lanthanide/counterion complex ($LnCI_3$), an uncharged organic amine (OA), and water. Once solubilized the lanthanide/counterion complex can be recovered from solution by any suitable means. For example, addition of a base that reacts with the lanthanide/counterion complex to form an insoluble lanthanide salt can be used to precipitate the extracted lanthanide from supernatant following removal of unreacted material. Alternatively, pH changes, temperature changes, or evaporation can be used to precipitate the solubilized lanthanide. In other embodiments, the lanthanide could be recovered by electrodeposition processes, such as electrowinning or electrorefining. In still other embodiments of the inventive concept the solubilized lanthanide can be recovered by ion exchange, for example using a fixed bed reactor or a fluidized bed reactor with appropriate media. It should be appreciated that the process of recovering the lanthanide can be selective, and that such selectivity can be utilized in the recovery of multiple lanthanides as described below.

The organic amine cation/counterion complex can be produced from the uncharged organic amine to regenerate the OA-H+/Cl- lixiviant, for example using an acid form of the counterion (H-Cl), as shown in Equation 2.

$$OA(aq)+H-Cl(aq)\rightarrow OA-H+(aq)+Cl- \quad \text{Equation 2}$$

In a preferred embodiment of the inventive concept the reaction described in Equation 2 can occur in parallel with the reaction described in Equation 1, for example by the addition of an acid form of the counterion (HCl) during the period in which the lixiviant is in contact with the sample.

It should be appreciated that an important feature of this process is the ability to exploit "chemical gain" through the regeneration of the lixiviant, in which the organic amine acts as a pseudocatalyst. This permits the use of substantially less than stoichiometric amounts of the lixiviant to recover all of the extractable active metal species as a soluble salt. Although it is not necessary to use less than the stoichiometric amount of lixiviant, doing so has the technical effects of reducing the environmental impact of such processes and of substantially reducing expense.

Organic amines suitable for the extraction of rare earth elements (for example from the ores monazite, bastnasite, xenotime and other materials) can have a pKa of about 7 to about 14, and can include protonated ammonium salts (i.e. not quaternary). Suitable organic amines can include ammonia, nitrogen containing organic compounds (for example monoethanolamine, diethanolamine, triethanolamine, morpholine, ethylene diamine, diethylenetriamine, triethylenetetramine, methylamine, ethylamine, propylamine, dipropylamines, butylamines, diaminopropane, triethylamine, dimethylamine, and trimethylamine), low molecular weight biological molecules (for example glucosamine, amino sugars, tetraethylenepentamine, amino acids, polyethyleneimine, spermidine, spermine, putrecine, cadaverine, hexamethylenediamine, tetraethylmethylenediamine, polyethyleneamine, cathine, isopropylamine, and a cationic lipid), biomolecule polymers (for example chitosan, polylysine, polyornithine, polyarginine, a cationic protein or peptide), and others (for example a dendritic polyamine, a polycationic polymeric or oligomeric material, and a cationic lipid-like material), or combinations of these. Such organic amines can range in purity from about 50% to about 100%. For example, an organic amine of the inventive concept can have a purity of about 50%, about 55%, about 60%, about 65%, about 70%, about 75%, about 80%, about 85%, about 90%, about 95%, about 97%, about 99%, or about 100%. In a preferred embodiment of the inventive concept the organic amine is supplied at a purity of about 90% to about 100%. It should be appreciated that such organic amines can differ in their ability to interact with different members of the lanthanide family and with contaminating species, and that such selectivity can be utilized in the recovery of multiple lanthanides as described below.

Inventors further contemplate that zwitterionic species can be suitable lixiviants, and note that such zwitterionic species can form cation/counterion pairs with two members of the same or of different molecular species. Examples include amine containing acids (for example amino acids and 3-aminopropanoic acid), chelating agents (for example ethylenediaminetatraacetic acid and salts thereof, ethylene glycol tetraacetic acid and salts thereof, diethylene triamine pentaacetic acid and salts thereof, and 1,2-bis(o-aminophenoxy)ethane-N,N,N',N'-tetraacetic acid and salts thereof), and others (for example betaines, ylides, and polyaminocarboxylic acids).

It is notable that the use of biologically derived organic amines is a sustainable practice, and has the beneficial effect of making this process more environmentally sound. In addition, it should be appreciated that some organic amines, such as monoethanolamine, have a reduced tendency to volatilize during processing than other organic amines, such as ammonia. In some embodiments of the inventive concept an organic amine can be a low volatility organic amine (i.e. having a vapor pressure less than or equal to about 1% that of ammonia under process conditions). In other embodiments of the inventive concept an organic amine can be a non-volatile organic amine (i.e. having a vapor pressure less than or equal to about 0.1% that of ammonia under process conditions). Capture and control of such low volatility and non-volatile organic amines requires relatively little energy and can utilize simple equipment. This reduces the likelihood of such low volatility and non-volatile organic amines escaping into the atmosphere and advantageously reduces the environmental impact of their use.

An example of an application of the inventive concept is in the isolation of insoluble cerium hydroxide from a monzanite ore that also includes an undesirable thorium impurity, using an ammonium chloride lixiviant. Equation 3 represents a reaction that takes place on contacting a monzanite process mud with an ammonium chloride lixiviant.

$$Ce(OH)_3(solid)+3NH_4+(aq)+3Cl-(aq)\rightarrow CeCl_3(aq)+3NH_3(aq)+3H_2O \quad \text{Equation 3}$$

Cerium is extracted from the ore as soluble cerium chloride (CeCl$_3$), with the generation of uncharged ammonia (NH$_3$) and water. The lixiviant is regenerated through the addition of hydrochloric acid (HCl), as shown in Equation 4.

$$NH_3(aq)+H+(aq)+Cl-(aq)\rightarrow NH_4+(aq)+Cl-(aq) \quad \text{Equation 4}$$

Advantageously, lixiviant can be regenerated during the extraction process by the addition of HCl. In such a process production of cerium chloride is controlled by the amount of lixiviant present relative to the amount of extractable metal ions, and the rate at which hydrochloric acid is added to the system. It should be appreciated that in such a process either the organic amine cation (ammonium salt) or the unprotonated organic amine (ammonia) can be used initially. Subsequently once the lixiviant has transferred its anion, fresh acid can be added to support the protonation of the organic amine so that further metal salt can be extracted. Since the protonation of the organic amine occurs in the solution phase, the reaction rate is much greater than direct contact of acid with solid metal oxide/hydroxide. The regenerated lixiviant can then undergo selective reaction with rare earth hydroxides according to Equation 3. In such a process cerium salts can be selectively extracted from process muds in a continuous manner via the reactions in Equation 3 and Equation 4 until all the cerium hydroxide is consumed or the addition of acid is ceased. The extent of reaction can be characterized conveniently by monitoring the pH of the reacting solution. Since thorium hydroxide in the process mud is not sufficiently basic to react with the lixiviant, the cerium hydroxide reacts preferentially and is extracted selectively by the lixiviant. As a result the thorium remains behind in the process mud.

It should be appreciated that systems, methods, and compositions of the inventive concept can also be used to selectively extract and/or refine a desired rare earth element (such as cerium) from an ore containing other contaminants, for example other rare earth elements. By using the lixiviants described herein, one skilled in the art can exploit the varying degrees of basicity associated with each rare earth element, and choose a lixiviant of corresponding acidity to achieve selective extraction.

It should be noted that the lixiviant allows for the selective extraction of cerium hydroxide in this example because it does not react with other metals or metal oxides/hydroxides of lower basicity that are found in the processing muds and solutions. For example zero valency metals (M0) are not reactive with the lixiviant, as shown in Equation 5).

$$M0(s)+NH_4+(aq) \rightarrow NO\ REACTION \qquad \text{Equation 5}$$

This selectivity is in contrast with prior art methods that do not utilize a lixiviant of the inventive concept, where acid will react nonselectively with zero valency metals (Equation 6), cerium hydroxide (Equation 7), and other potential metal oxides/hydroxides, for example thorium oxide (Equation 8).

$$2M0(s)+6H+(aq) \rightarrow 2M3+(aq)+3H_2(g) \qquad \text{Equation 6}$$

$$Ce(OH)_3(s)+3H+(aq) \rightarrow Ce3+(aq)+3H_2O \qquad \text{Equation 7}$$

$$ThO_2(s)+4H+(aq) \rightarrow Th4+(aq)+2H_2O \qquad \text{Equation 8}$$

The use of the lixiviant in this pseudo-catalytic manner, acts as a proton shuttle allowing for the selective reaction with, in this example but not limited to, cerium hydroxide.

The soluble cerium salt, for example cerium chloride from Equation 3, and the soluble ammonia from Equation 3 (or soluble ammonium ion if the reaction is metal oxide/hydroxide limited) can easily be separated from the insoluble solid residue. Once separated, the soluble aqueous fraction can be used as-is if the target process can tolerate the small quantity of ammonia or ammonium chloride as a contaminant. Alternatively, the solution can be further processed as needed.

Figure 1:
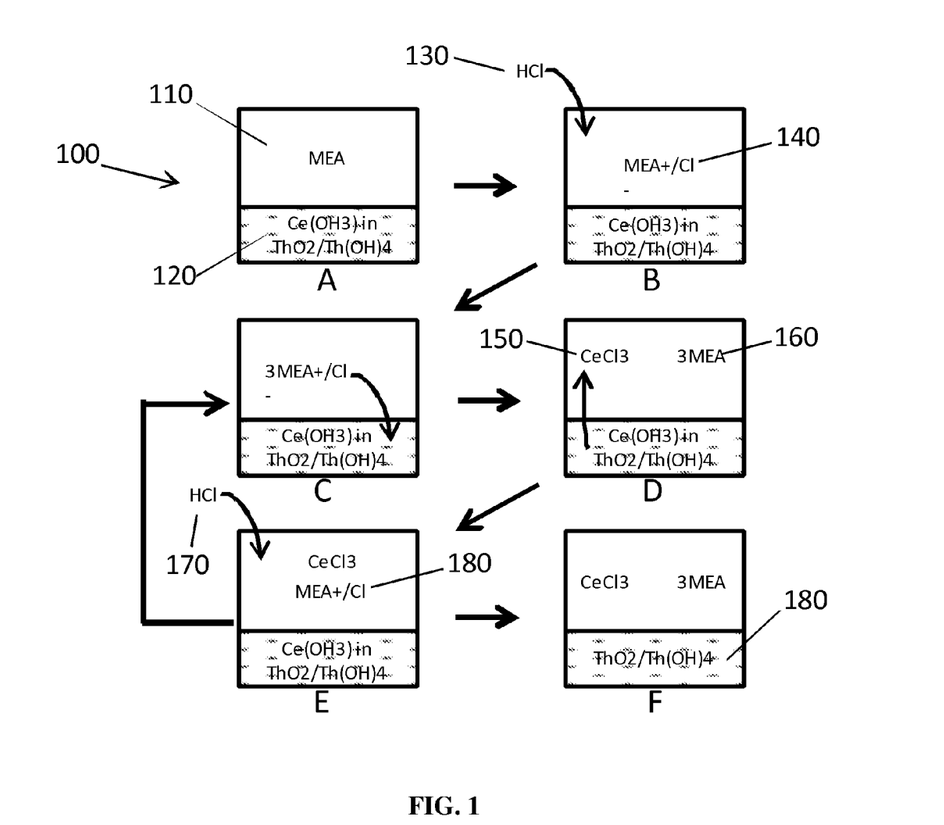
FIG. 1A to FIG. 1F depict an example of a method of the inventive concept in which cerium is recovered from a thorium contaminated sample, using an organic amine chloride lixiviant that is regenerated.

As noted above, in some instances the use of a low volatility and/or non-volatile lixiviant is desirable. An example of such a process of the inventive concept is the extraction of cerium (Ce) from an ore using a non-volatile organic amine, such as monoethanolamine hydrochloride, as shown in FIG. 1A to FIG. 1F. As shown in FIG. 1A, a tank 100 or other suitable arrangement includes an aqueous solution of an organic amine 110 (in this instance monoethanolamine) and a mud or slurry 120 containing cerium hydroxide ($Ce(OH)_3$), thorium oxide ($ThO_2$) and thorium hydroxide ($Th(OH)_4$). The extraction process can be initiated as shown in FIG. 1B by the addition of an acid form of a counterion 130, in this instance hydrochloric acid (HCl), which generates an organic acid cation/counterion pair 140 (in this instance monoethanolamine hydrochloride (MEA+/Cl−)). Monoethanolamine hydrochloride (MEA.HCl, $HOC_2H_4NH_3Cl$) conforms to Compound 1 as follows: one nitrogen atom ($N_1$) is bound to one carbon atom ($R_1=C_2H_5O$) and 3 hydrogen atoms ($R_2$, $R_3$ and H), and there is one chloride counteranion ($X_1=Cl−$). As shown in FIG. 1C this compound, when dissolved in water or another suitable solvent, can enter or mix with the mud/slurry and, as shown in FIG. 1D, effectively extract a rare earth hydroxide, for example cerium hydroxide ($Ce(OH)_3$), by the formation of a soluble rare earth cation/counterion pair 150 (in this instance, cerium chloride ($Ce(Cl)_3$)). Equation 9 depicts a critical chemical reaction in such an extraction (in this case cerium, from an alkaline opened mined ore source with significant thorium content). Note that MEA.HCl dissociates in water into monoethanolammonium cation ($HOC_2H_4NH_3+(MEAH+)$) and chloride anion (Cl−).

$$Ce(OH)_3(s)+3HOC_2H_4NH_3+(aq)+3Cl-(aq) \rightarrow \\ CeCl_3(aq)+3HOC_2H_4NH_2(aq)+3H_2O(l) \qquad \text{Equation 9}$$

As illustrated in FIG. 1D, this process also generates an uncharged organic amine 160, in this instance monoethylamine (MEA). The organic amine cation/counterion pair 180 can be regenerated, as shown in FIG. 1E, from the reaction products of equation 9 by the addition of the corresponding acid 170 (in this instance HCl), as shown in Equation 10.

$$HOC_2H_4NH_2(aq)+HCl(aq) \rightarrow HOC_2H_4NH_3+(aq)+Cl- \qquad \text{Equation 10}$$

This process can be repeated, eventually leading to the depletion of the rare earth element from the mud or slurry, which retains the unwanted thorium contaminants 180 as shown in FIG. 1F.

As in the example utilizing ammonium chloride, this process advantageously utilizes "chemical gain", in which the MEA.HCl acts as a pseudocatalyst. One can use substantially less than stoichiometric amounts of the lixiviant to recover all of the desired extractable active metal species as a soluble salt. This has both economic and environmental benefits and, additionally, simplifies any necessary subsequent product purification steps.

The metal salt production is controlled by the amount of lixiviant present relative to the amount of extractable metal ions, and the rate of acid added to the system. When first starting the process either the ammonium salt or the unprotonated organic amine may first be used. Subsequently once the anion is consumed, fresh acid can be added to provide protonation of the organic amine so that further metal salt can be produced. Because the protonation of the organic amine occurs in exclusively in the solution phase, the reaction rate is much greater than direct contact of acid with metal oxide. The regenerated lixiviant can then undergo selective reaction with cerium hydroxide according to Equation 9. In this manner, cerium can selectively be extracted from waste material in a continuous manner via the reactions in Equation 9 and Equation 10 until all the cerium hydroxide is consumed or addition of acid is ceased.

It should be reiterated that the lixiviant allows for the selective extraction of cerium in this example because it does not react with other metals or metal oxides/hydroxides in the monazite process mud slag (e.g. thorium oxide does not react with the lixiviant, see Equation 11).

$$ThO2(s)+HOC_2H_4NH_3+(aq) \rightarrow NO\ REACTION \qquad \text{Equation 11}$$

Whereas, in the absence of the lixiviant, the acid will react unselectively with thorium oxide (Equation 8) and cerium hydroxide (Equation 8), as well as other potential metals and metal oxides/hydroxides.

The soluble cerium salt and the soluble MEA from Equation 9 (or soluble MEAH+ if reaction is metal oxide/hydroxide limited) can easily be separated from the insoluble solid residue. Once separated, the soluble aqueous fraction can used as-is if the target process can withstand the small quantity of lixiviant as a contaminant, or the solution can be furthered processed as needed.

The rare earth element containing solution can be concentrated or diluted to a desired strength as required by the end user. Alternatively, the solution can be boiled down or evaporated completely, leaving a rare earth element chloride and/or various hydrates thereof, depending on how vigorously the mixture is dried. The residual uncharged organic amine could also be removed by this process and optionally captured for reuse. The dried rare earth element chlorides could be further processed into oxides via thermal oxidation, precipitation with agents such oxalic acid, sodium hydroxide, potassium hydroxide or other precipitating agents.

In another embodiment of the inventive concept mixture of rare-earth hydroxides can be extracted for further refinement. In such an embodiment an organic amine lixiviant and reaction conditions can be selected that produce a mixture of rare earth element cation/counterion pairs in solution and leaves undesired contaminants in the insoluble slag. The mixture of rare earth element cation/counterion pairs could be separated from residual lixiviant by, for example, precipitation with a hydroxide. Alternatively, rare earth element salts could be recovered by drying or other solvent removal technique. In such an approach a relatively volatile lixiviant (such as, for example, ammonia) can be selected to simplify removal and recovery of the organic amine. The most basic rare earth element present (for example, lanthanum hydroxide) can be selectively extracted by exposing the rare earth element hydroxide mixture precipitate to an amount of a second amine-based lixiviant that is just acidic enough for the lanthanum to be selectively extracted. The resulting solution could then be concentrated or diluted to a desired strength as required by downstream processes.

There are of course many possible lixiviants of the form of Compound 1, and there are likewise many organic amines and rare earth element sources. While the examples provided have described the action of two organic amine lixiviants (i.e. ammonium chloride and monoethanolamine hydrochloride (a.k.a. monoethanolammonium chloride) with one particular cerium source, (monazite) other examples of process of the inventive concept can utilize organic amine cation/counterion pairs such as ammonium acetate, monoethanolammonium acetate, ammonium nitrate, or monoethanolammonium nitrate. Alternatively, biologically derived lixiviants such as the amino acid glycine (or a salt of itself) or the hydrobromide salt of poly-L-lysine can be used. Similarly, while examples note the use of monazite ore, other ores (such as xenotime, euxenite, allanite, loparite, samarskite, aeschynite, fergusonite, parasite, synchisite, tengerite, ancylite, florencite, britholite, thalenite, gadolinite, and eudialyte) are suitable. Alternatively, systems, methods, and compositions of the inventive concept can be utilized to recover rare earth elements from electronic waste, consumer waste, industrial waste, scrap or other excess materials from manufacturing processes, or other post-utilization sources. Any source that contains a basic form of a rare earth metal can be suitable. For example alkali-processed monazite sands that contain thorium compounds can be used as a source material in methods of the inventive concept. In preferred embodiments the rare earth source is a rare earth hydroxide that can be separated from a matrix using an acid, for example HCl.

Many rare earth elements on the periodic table can form hydroxides; most of these have very limited solubility in water. These hydroxides also have varying degrees of basicity. While cerium (III) hydroxide as produced from various mineral sources has been cited as an example there are many other rare earth elements that form suitable bases in water. Examples of other elements that, in hydroxide form, are suitable for use in systems and methods of the inventive concept include scandium, yttrium, lanthanum, praseodymium, neodymium, promethium, samarium, europium, gadolinium, terbium, dysprosium, holmium, erbium, thulium, ytterbium, and leutetium. Such salts have different basicities, which can be paired with organic amine based lixiviants of different acidities to provide selective recovery.

It should also be noted that systems, methods, and compositions of the inventive concept are not limited to one metal species being extracted with one particular lixiviant or set of anions. Multiple metal species with various organic amine based lixiviants and various anions (or acids) can be used in sequence or in parallel to extract a particular mixture of metals or to produce a particular mixture of metal salts.

As described above, lixiviants of the inventive concept can be applied in a variety of methods. Examples of some of these methods are depicted schematically in FIG. 2, FIG. 3, and FIG. 4.

Figure 2:
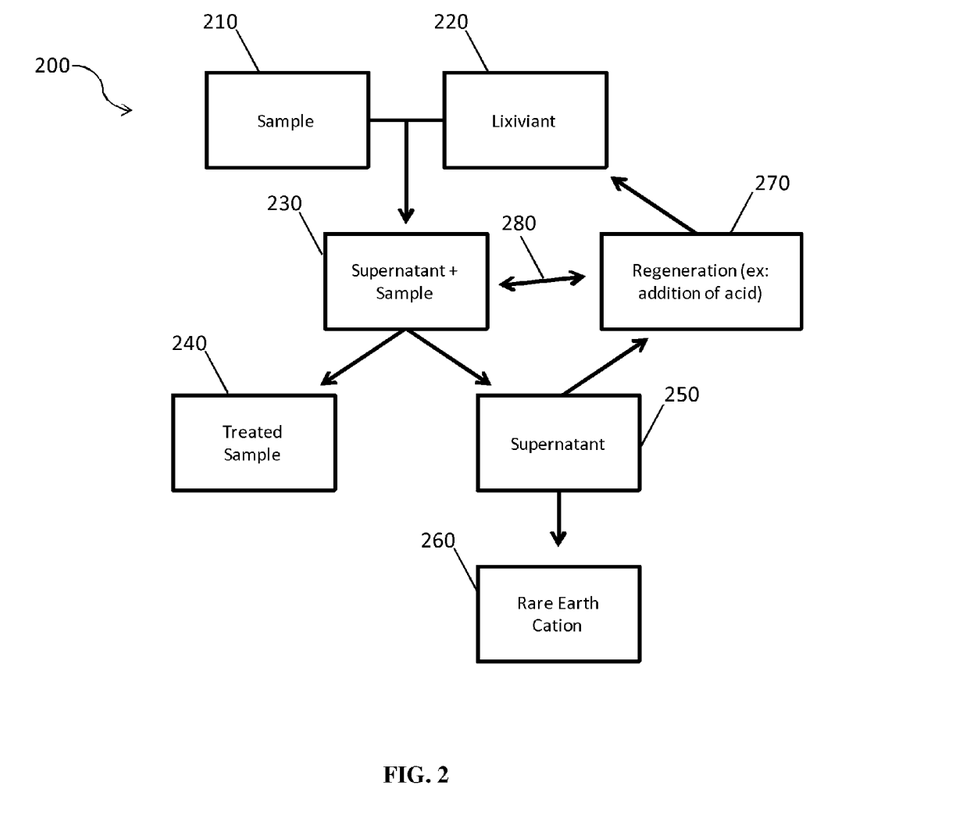
FIG. 2 schematically depicts a method of the inventive concept, in which a rare earth elements is recovered from an ore using a lixiviant, which is regenerated.

FIG. 2 depicts a method of the inventive process 200 in which a sample 210, for example an ore or other source or rare earth metal, is mixed with a lixiviant 220. The lixiviant can include a solvent and one or more organic amine species as described above in the form of a cation, coupled with a suitable counterion (for example, chlorine and/or other halides). Suitable solvents include any protic or highly polar solvent, or any solvent that can solvate large amounts of rare earth metal salts. In preferred embodiments of the inventive concept the solvent is water, a glycol, or a water/glycol mixture.

The organic amine component of the lixiviant can be chosen based on selectivity, efficiency, or economic considerations. Suitable organic amine species can be described by Compound 1, above. In some embodiments the organic amine can be a bromide, chloride, acetate, or nitrate salt of diethanolamine or triethanolamine. In other embodiments the organic amine can be a chloride or acetate salt of an amino acid, for example glycine or lysine. In preferred embodiments of the inventive concept the organic amine can be ammonium chloride or monoethanolamine chloride. Similarly, the concentration of organic amine can be selected for optimal or improved performance. As noted above the organic amine can be utilized in substoichiometric amounts, however this is not a requirement. For example, a monovalent organic amine can be used at concentrations and volumes that give about a molar ratio of about 0.01 to about 3.05 relative to the amount of available rare earth metal in the sample. In such an embodiment higher organic amine to rare earth element molar ratios can be utilized in batch processing operations, in which the lixiviant is not constantly regenerated through the addition of acid.

The sample 210 can be treated physically and/or chemically prior to mixing with the lixiviant 220. For example, the components of the sample 210 can be reduced in size, for example through milling, grinding, pulverizing, or sifting. In some embodiments components of the sample can have a mean diameter of about 0.005 mm to about 1 mm after such processing. In other embodiments components of the sample can have a mean diameter of about 0.01 mm to about 0.25 mm after such processing. In preferred embodiments of the inventive concept components of the sample can have a mean diameter of about 0.025 mm to about 0.125 mm. Such processes improve the surface area to volume ratio of elements of the sample and can serve to increase reaction rates. In some embodiments a sample can be chemically treated, for example through exposure to strong bases (such as sodium hydroxide), heating, oxidation, or a combination of these. Such chemical treatments can serve to generate rare earth metal salts (for example, hydroxides or oxides) or to alter the physical structure of the sample or components of the sample.

On interacting with the lixiviant 220, rare earth elements in the sample interact with organic amine cations and counterions to form a soluble rare earth element cation/counterion complex that is solubilized in the supernatant 230, along with an uncharged organic amine. This extraction process can be rapid, reaching completion in about 0.5 hours to about 24 hours. In preferred embodiments the extraction time is from about 2 hours to about 4 hours. The mass ratio of rare earth element to solvent can be adjusted to improve process efficiency. In some embodiments the ratio of rare earth element to solvent ratio is about 0.02 to about 0.5. In other embodiments the ratio of rare earth element to solvent is about 0.05 to about 0.25. In preferred embodiments of the inventive concept the ratio of rare earth element to solvent is about 0.1 to about 0.15.

Other parameters can be adjusted during the extraction process in order to optimize the selectivity and efficiency of the extraction process, for example temperature and mixing speed. In some embodiments the temperature during extraction can be from about 0° C. to about 200° C. In other embodiments the temperature during extraction is about 50° C. to about 150° C. In a preferred embodiment of the inventive concept the temperature during extraction is about 150° C. Similarly, during extraction the mixture of sample and lixiviant can be stirred at about 100 rpm to about 2000 rpm. In preferred embodiments the mixture of sample and lixiviant can be stirred at about 200 rpm to about 500 rpm.

In the extraction process unwanted contaminants are not solvated by the lixiviant, and remain behind as insoluble material, for example as a treated sample 240 that can be further processed if desired. The pH of the lixiviant can change during the extraction process, ranging from about pH 6 to about pH 13 at the beginning of the extraction, and from about pH 6 to about pH 9 at the end of the extraction process. Such pH changes can provide an indication of the progress of the reaction, or, alternatively, can be used to indicate a need to regenerate the lixiviant. The supernatant 250 can be separated from the insoluble materials of the treated sample 240 by a variety of processes, including settling, filtration, or centrifugation, either alone or in combination. The rare earth cation 260 can be recovered from the supernatant 250 by any suitable means, including electrodeposition, precipitation (for example, by the addition of a base such as hydroxide), and ion exchange. In a preferred embodiment insoluble materials are removed by filtration. In such embodiments the efficiency of the process can be improved by washing the filter cake of insoluble material to recover additional lixiviant containing solubilised rare earth elements, however this must be weighed against the impact of dilution on subsequent steps. In some embodiments the filter cake is washed with a liquid volume of about 10 times the volume of the cake wetness. In other embodiments the filter cake is washed with a liquid volume of about 5 times the volume of the cake wetness. In preferred embodiments the filter cake is washed with a liquid volume of about 3 times the volume of the cake wetness.

The uncharged organic amine remaining in the supernatant 250 can, in turn, be regenerated 270 to form an organic amine cation that can form part of a lixiviant 220 that can be used in the next cycle of the reaction. For example, if a supernatant 250 is treated with an acidic form of the counterion of the lixiviant 220, the uncharged organic amine can be converted to an organic amine cation/counterion pair that can be used as a lixiviant 220 in the next application of the method. In preferred embodiments of the organic concept, an acidic form of the counterion can be added to the mixed first supernatant and sample 230 to regenerate the charged organic amine/counterion pair in situ 280. The acid used for regeneration can be any acid that is able to maintain the rare earth salt solubility in the lixiviant, for example HBr, HCl, or acetic acid. In a preferred embodiment the acid is HCl. It should be appreciated that in such an embodiment the organic amine can act as a pseudocatalyst, serving to shuttle counterions to rare earth element components of the sample while not being consumed. This advantageously permits the use of the organic amine in substochiometric amounts relative to the rare earth element content of the sample, which limits both the environmental impact of such operations and permits considerable savings in materials.

Figure 3:
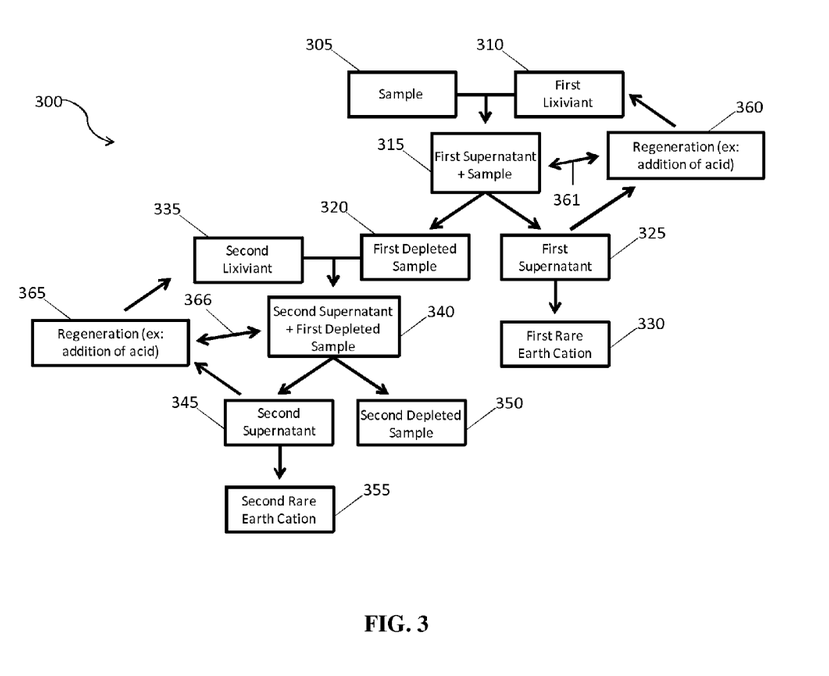
FIG. 3 schematically depicts another method of the inventive concept, in which different rare earth elements are recovered in a stepwise fashion.

Other embodiments of the inventive concept can advantageously utilize the selective complex formation and solubility of components of methods of the inventive concept to recover different rare earth elements from the same sample. One example of such a method is shown in FIG. 3. As shown, such a method can be a chain of reactions that are, essentially, one or more repetitions of the method shown in FIG. 1 applied to a progressively depleted sample. In an example of such a method 300, a sample 305 and a first lixiviant 310 are brought into contact with each other. The first lixiviant 310 includes a first organic amine cation and a counterion, and reaction 315 with the sample 305 produces a first depleted sample 320 and a first supernatant 325 that includes a first rare earth cation, a counterion, and an uncharged organic amine. The first depleted sample 320 includes materials that were not reactive with the first lixiviant, which can include additional rare earth elements, other valuable materials, and unwanted contaminants. It can be separated from the first supernatant 325 by any suitable method, including settling, filtration, and centrifugation, either alone or in combination. The first rare earth cation 330 can be recovered from the first supernatant 325 by any suitable means, including electrodeposition, precipitation (for example, by the addition of a base such as hydroxide), and ion exchange. The uncharged first organic amine remaining in the supernatant 325 can, in turn, be regenerated 360 to give a first organic amine cation that can form part of a first lixiviant 310 that can be used in the next cycle of the reaction. The first depleted sample 320 can, in turn, be contacted 340 with a second lixiviant 335 that includes a second organic amine cation/counterion pair. Reaction with the first depleted sample 240 produces a second depleted sample 350 and a second supernatant 345 that includes a soluble second rare earth element cation/counterion complex and uncharged second organic amine. The second rare earth cation 355 can be recovered from the second supernatant 345 by any suitable means, including precipitation (for example, by treatment with a base that forms an insoluble salt), electrodeposition, and/or ion exchange. Uncharged second organic amine can be treated 365, for example with an acid form of the counterion, to regenerate the second lixiviant 335. In some embodiments of the inventive concept the second depleted sample 350 is subjected to further rounds of treatment with lixiviants in order to recover additional valuable materials. It should be appreciated that, as described in the process illustrated in FIG. 2, that an acid form of the counterion can be added to the mixtures of lixiviant and sample to regenerate the first organic amine cation 361, the second organic amine cation 366, or both the first and second organic amine cations 361, 366 in situ, permitting them to act as pseudocatalysts and permitting the first organic amine, the second organic amine, or both the first and second organic amine to be used in substochiometric quantities. This advantageously permits the use of the organic amine in substochiometric amounts relative to the rare earth element content of the sample, which limits both the environmental impact of such operations and permits considerable savings in materials.

Figure 4:
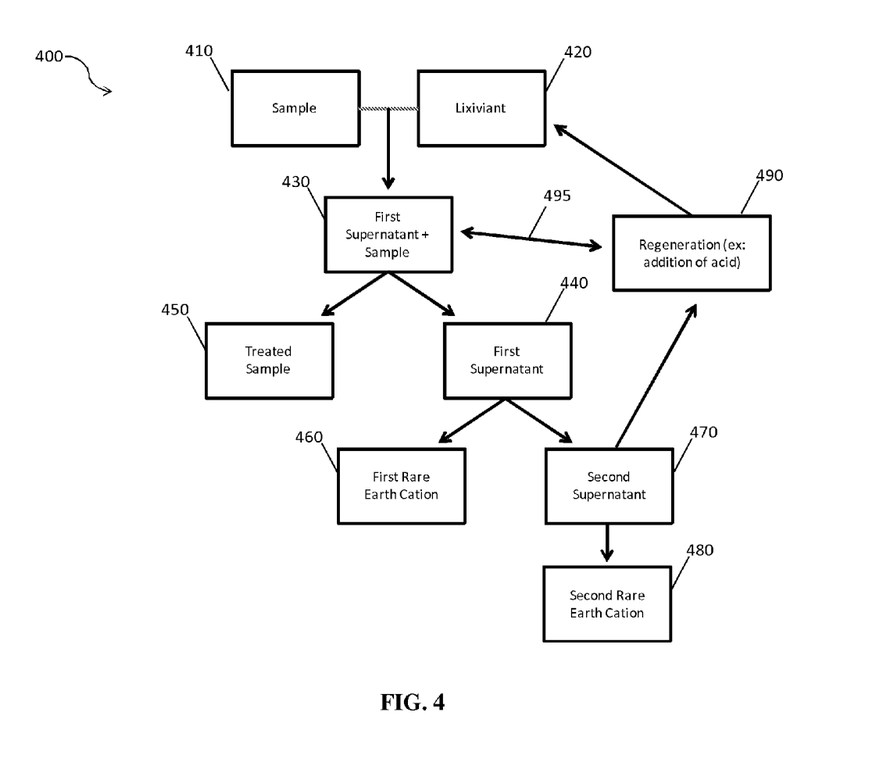
FIG. 4 schematically depicts an alternative embodiment of the inventive concept, in which different rare earth elements are recovered in a stepwise manner.

Another embodiment of the inventive concept that permits recovery of two or more rare earth elements from a sample is shown in FIG. 4. In such a method 400 a sample 410 is contacted with a lixiviant 420 that includes a first organic amine cation/counterion pair and a second organic amine cation/counterion pair. This mixture 430 results in a treated sample 450 and a first supernatant 440. This first supernatant can include a first rare earth element cation/counterion pair, a second rare earth element cation/counterion pair, a first uncharged organic amine, and a second uncharged organic amine. The first rare earth cation 460 can be recovered from the first supernatant 440 by any suitably selective means, including precipitation with a first precipitant (for example, by treatment with a base that forms an insoluble salt), electroplating, or ion exchange. Recovery of the first rare earth cation 460 from the first supernatant 440 yields a second supernatant 470, which includes a second rare earth element cation/counterion pair, an uncharged first organic amine, and an uncharged second organic amine. The second rare earth cation 480 can be recovered from the second supernatant 470 by any suitable means, such as precipitation with a second precipitant (for example, through treatment with additional amounts of a base that forms an insoluble salt), electrodeposition, or ion exchange. Following extraction of rare earth elements, the second supernatant 470 can be treated (for example, by the addition of an acid form of the counterion) to regenerate the lixiviant 420. In some embodiments of the inventive concept the first organic amine and the second organic amine (and their respective cations) can be different molecular species with different acidities and/or specificities for rare earth elements. In other embodiments of the inventive concept the first organic amine and the second organic amine can be the same molecular species, with selectivity between the first rare earth element and the second rare earth element being provided by the method used for their recovery from supernatants. For example, in some embodiments the first precipitant and the second precipitant are different species that selectively precipitate the first and second rare earth elements, respectively. Alternatively, in other embodiments the first precipitant and the second precipitant are the same species utilized under different conditions, for example at different concentrations and/or temperatures. It should be appreciated that, as described in the processes illustrated in FIG. 2 and FIG. 3, that an acid form of the counterion can be added to the mixtures of lixiviant and sample to regenerate the first organic amine cation, the second organic amine cation, or both the first and second organic amine cations in situ 495, permitting them to act as pseudocatalysts and permitting the first organic amine, the second organic amine, or both the first and second organic amine to be used in substochiometric quantities. This advantageously permits the use of the organic amine in substochiometric amounts relative to the rare earth element content of the sample, which limits both the environmental impact of such operations and permits considerable savings in materials.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for extracting a rare earth element, comprising:
    contacting a sample comprising a first rare earth element with a first lixiviant, the first lixiviant comprising a first organic amine cation and a first counterion;
    forming a first supernatant comprising an uncharged first organic amine, and a first complex comprising a cation of the first rare earth element and the first counterion;
    transferring the first rare earth element cation from the first supernatant; and
    regenerating the first organic amine cation,
    wherein the first organic amine cation is provided in substoichiometric amounts relative to the first rare earth element.

2. The method of claim 1, wherein the first organic amine cation is regenerated by the addition of an acid form of the first counterion while the sample is in contact with the first lixiviant.

3. The method of claim 1, further comprising the step of removing the first complex from the supernatant.

4. The method of claim 3, wherein the first complex is removed by forming a precipitate.

5. The method of claim 1, wherein the first organic amine cation has a pKa of 8 to 14.

6. The method of claim 5, wherein the first organic amine cation is obtained from a biological source.

7. The method of claim 1, wherein the first counterion has a pKa of 1 to 6.

8. The method of claim 1, wherein the first lixiviant is formed by adding an acid to the uncharged first organic amine that is in contact with the sample.

9. The method of claim 1, wherein the first rare earth element cation is transferred by forming a precipitate.

10. The method of claim 1, wherein the sample further comprises a second rare earth element, and further comprising the steps of:
    transferring the first supernatant from the sample to form a depleted sample;
    contacting the depleted sample with a second lixiviant, the second lixiviant comprising a second organic amine cation and a second counterion;
    forming a second supernatant comprising an uncharged second organic amine and a second complex comprising a second rare earth element cation and the second counterion
    transferring the second rare earth element cation from the second supernatant; and,
    regenerating the second organic amine cation.

11. The method of claim 10, wherein the second organic amine cation is regenerated by addition of an acid form of the second counterion while the sample is in contact with the second lixiviant.

12. The method of claim 10, wherein the second rare earth element cation is transferred by forming a precipitate.

13. A method for extracting rare earth elements, comprising:
contacting a sample comprising a first rare earth element and a second rare earth element with a lixiviant, the lixiviant comprising an first organic amine cation, a second organic amine cation, and a counterion;
forming a first supernatant comprising an uncharged first organic amine, an uncharged second organic amine, a first complex comprising a first rare earth metal cation and the counterion, and a second complex comprising a second rare earth metal cation and the counterion;
transferring the first rare earth metal cation from the first supernatant to form a second supernatant;
transferring the second rare earth metal cation from the second supernatant and,
regenerating the first organic amine cation and the second organic amine cation from the second supernatant,
wherein the first organic amine cation is provided in substoichiometric amounts relative to the first rare earth metal.

14. The method of claim 13, wherein the first organic amine cation has a pKa of 8 to 14.

15. The method of claim 13, wherein the second organic amine has a pKa of 8 to 14.

16. The method of claim 13, wherein the first organic amine cation and the second organic amine cation are identical chemical species.

17. The method of claim 13 wherein the first organic amine cation and the second organic amine cation are different species.

18. The method of claim 13, wherein the first organic amine cation is regenerated by the addition of an acid form of the counterion while the sample is in contact with the lixiviant.

19. The method of claim 13, wherein the first rare earth element is transferred from the first supernatant by the addition of a first precipitant.

20. The method of claim 19, wherein the first precipitant is a base comprising a hydroxide.

21. The method of claim 19, wherein the second rare earth element is transferred from the second supernatant by addition of a second precipitant.

22. The method of claim 21, wherein the first precipitant and the second precipitant are identical chemical species applied to give a first concentration of the species in the first supernatant and a second concentration of the species in the second supernatant.

* * * * *